(12) United States Patent
Castillo Bocanegra et al.

(10) Patent No.: US 10,239,842 B2
(45) Date of Patent: Mar. 26, 2019

(54) HYDROSOLUBLE COMPOUNDS DERIVED FROM BENZIMIDAZOLE USED IN TREATING FASCIOLOSIS

(71) Applicant: UNIVERSIDAD NACIONAL AUTONOMA DE MEXICO, Mexico City (MX)

(72) Inventors: Rafael Castillo Bocanegra, Mexico City (MX); Miguel Angel Flores Ramos, Mexico City (MX); Maria Alicia Hernandez Campos, Mexico City (MX); Osvaldo Froylan Ibarra Velarde, Mexico City (MX); Remedios Yolanda Vera Montenegro, Mexico City (MX)

(73) Assignee: UNIVERSIDAD NACIONAL AUTONOMA DE MEXICO, Mexico City (MX)

( * ) Notice: Subject to any disclaimer, the term of this patent is extended or adjusted under 35 U.S.C. 154(b) by 0 days.

(21) Appl. No.: 15/529,218

(22) PCT Filed: Nov. 25, 2015

(86) PCT No.: PCT/MX2015/000154
§ 371 (c)(1),
(2) Date: May 24, 2017

(87) PCT Pub. No.: WO2016/085319
PCT Pub. Date: Jun. 2, 2016

(65) Prior Publication Data
US 2017/0327470 A1    Nov. 16, 2017

(30) Foreign Application Priority Data
Nov. 26, 2014  (MX) .................. MX/a/2014/014417

(51) Int. Cl.
*A61K 31/675* (2006.01)
*A61K 31/4184* (2006.01)
*C07D 235/28* (2006.01)
*C07F 9/09* (2006.01)
*A61K 31/66* (2006.01)
*C07F 9/6506* (2006.01)

(52) U.S. Cl.
CPC ........ *C07D 235/28* (2013.01); *A61K 31/4184* (2013.01); *A61K 31/66* (2013.01); *A61K 31/675* (2013.01); *C07F 9/09* (2013.01); *C07F 9/65068* (2013.01)

(58) Field of Classification Search
CPC ....... C07D 235/28; C07F 9/09; A61K 31/675; A61K 31/4184
USPC .............. 548/307.1, 310.1, 113; 514/395, 80
See application file for complete search history.

(56) References Cited

U.S. PATENT DOCUMENTS 7,893,271 B2    2/2011  Chassaing

FOREIGN PATENT DOCUMENTS

WO    199312124 A1    6/1993
WO    2007014846 A1    2/2007

OTHER PUBLICATIONS

Flores-Ramos, M., F. Ibarra-Velarde, A. Hernandez-Campos, Y. Vera-Montenegro, H. Jung-Cook, G. Canto-Alarcon, L. Misael del Rivero and R. Castillo, "A highly water soluble benzimidazole derivative userful for the treatment of fasciolosis" Bioorg. & Med. Chem. (2014), 24 (24), pp. 5814-5817. (Year: 2014).*
Coles, "Anthelmintic activity of triclabendazole", Journal of Helminthology, vol. 60, No. 3, 1986, pp. 210-212.
Güralp et al., "Trematodiasis in Turkey: comparative efficacy of triclabendazole and niclofolan against natural infections of Fasciola hepatica and F. gigantica in sheep", Journal of Helminthology, vol. 58, No. 2, 1984, pp. 113-116.
Fairweather, "Triclabendazole: new skills to unravel an old(ish) enigma", Journal of Helminthology, vol. 79, No. 3, 2005, pp. 227-234.
Overend et al., "Resistance of Fasciola hepatica to triclabendazole", Australian Veterinary Journal, vol. 72, No. 7, Jul. 1995, pp. 275-276.
Smeal et al., "The activity of triclabendazole against immature and adult fasciola hepatica infections in sheep", Australian Veterinary Journal, vol. 60, No. 11, Nov. 1983, pp. 329-331.
Winkelhagen et al., "Apparent Triclabendazole-Resistant Human Fasciola hepatica Infection, the Netherlands", Emerging Infectious Diseases, vol. 18, No. 6, Jun. 2012, pp. 1028-1029.

(Continued)

*Primary Examiner* — Matthew P Coughlin
*Assistant Examiner* — Sagar Patel
(74) *Attorney, Agent, or Firm* — Shumaker, Loop & Kendrick, LLP

(57) ABSTRACT

The present invention relates to hydrosoluble compounds derived from benzimidazole represented by general formula I:

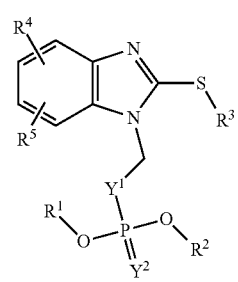

Formula (I)

wherein:
$Y^1$ e $Y^2$ are independently O or S, and at least one of $Y^1$ and $Y^2$ is O; $R^1$ and $R^2$ are independently hydrogen or a cation, both are hydrogen or both are cations; $R^3$ is a C1-4 alkyl; $R^4$ and $R^5$ are independently halogen or a —$OR^6$ alkoxide; $R^6$ is C6-C10 aryl linked in 5- or 6-position of benzimidazole nucleus.

20 Claims, No Drawings

(56) References Cited

OTHER PUBLICATIONS

Wolff et al., "Efficacy of Triclabendazole Against Fasciola Hepatica in Sheep and Goats", Veterinary Parasitology, vol. 13, No. 2, Sep. 1983, pp. 145-150.
World Congress on Diseases of Cattle; Coubrough, R.I.; World Associate for Buiatrics Hyman WB, Es, "Proceedings: XIIIth World Congress on Diseases of Cattle: Durban, Republic of South Africa World Buiatrics Association" dated Sep. 17-21, 1984, vol. 1, pp. 422-426.
Mantyla et al., "A novel synthetic route for the preparation of alkyl and benzyl chloromethyl phosphates", Tetrahedron Letters, vol. 43, Issue 21, dated May 20, 2002, pp. 3793-3794.
Boray et al., "Treatment of immature and mature Fasciola hepatica infections in sheep with triclabendazole", The Veterinary Record, Oct. 1, 1983, pp. 315-317.
Turner et al., "Anthelmintic efficacy of triclabendazole against Fasciola hepatica in sheep", The Veterinary Record, Jan. 14, 1984, pp. 41-42.
Foreyt, "Efficacy of triclabendazole against experimentally induced Fascioloides magna infections in sheep", Am. J. Vet. Res., vol. 50, No. 3, Mar. 1989, pp. 431-432.
Fairweather, et al., "Fasciolicides: Efficacy, Actions, Resistance and its Management", The Veterinary Journal, vol. 158, No. 2, 1999, pp. 81-112.
Mas-Coma et al., "Epidemiology of human fascioliasis: a review and proposed new classificaiton", World Health Organization, vol. 77, No. 2, dated 1999, pp. 340-346.
Hernandez-Campos et al., "Synthesis and Fasciolicidal Activity of 5-Chloro-2-methylthio-6-(1-naphthyloxy)-1H-benzimidazole", Chem. Pharm. Bull. vol. 50, No. 5, May 2002, pp. 649-652.
Fairweather, "Triclabendazole progress report, 2005-2009: an advancement of learning?", Journal of Helminthology, vol. 83, May 2009, pp. 139-150.
McConville et al., "An evaluation of the efficacy of compound alpha and triclabendazole against two isolates of Fasciola hepatica", Veterinary Parasitology vol. 162, May 2009, pp. 75-88.
Villegas et al., "Adminstration of Triclabendazole Is Safe and Effective in Controlling Fascioliasis in an Endemic Community of the Bolivian Altiplano", Pilot Fascioliasis Control Intervention in Bollivia, vol. 6, No. 8, Aug. 2012, pp. 1-7.
Written Opinion and International Search Report for PCT/MX2015/000154 dated Apr. 22, 2016, along with Translation (14 pgs.).
Romero et al., "Research Progress in Fasciolosis", National Autonomous University of Mexico, Faculty of Veterinary Medicine and Zootechnics Parasitology Department, vol. 1, 2000 (17 pages).

* cited by examiner

HYDROSOLUBLE COMPOUNDS DERIVED FROM BENZIMIDAZOLE USED IN TREATING FASCIOLOSIS

FIELD OF THE INVENTION

The present invention is related to principles and techniques used in Veterinary Pharmaceutical Industry for developing new pharmaceutical compositions for manufacturing medicaments which contribute to animal health, and more specifically, it relates to new hydrosoluble compounds derived from benzimidazole useful in treatment of fasciolosis in domesticated and wild animals, as well as in humans, and is also related to a pharmaceutical composition including said new hydrosoluble compounds.

BACKGROUND OF INVENTION

Fascioliasis or fasciolosis is a parasitary disease (helminthiasis) caused by two species of digenetic trematodes *Fasciola hepatica* and *Fasciola gigantica*, commonly known as liver flukes. These are localized in adults in biliary vesicle or in liver biliary ducts.

Fasciolosis causes large losses in livestock and in the economics of producing countries of domesticated animals and their products, such as milk, meat, wool, hide, etc. It also affects to cattle, sheep and goats, but it may be also present in wild animals, and sometimes in humans; therefore the infection is considered a zoonosis which is a severe worldwide problem.

Epidemiologic status of human fasciolosis has changed in recent years. Since 1980 the number of persons infected by *Fasciola hepatica* has significantly increased, and in several geographic zones true human endemics have been disclosed, with low to very high figures of prevalence and intensity. Prevalence zones for fasciolosis in humans do not necessarily match with zones wherein the disease constitutes a first order veterinary problem.

Fasciolosis may no longer be simply considered as a secondary zoonotic disease, but as a significant parasitic human disease (Bulletin of World Health Organization 1999, Mas-Coma). Fasciolosis is a global disease and human cases have been registered in more than 75 countries worldwide. Zones which are known for high transmission are South America highlands, Nile Valley, Caspian Sea basin extended between Europe and Asia, and also Eastern Asia, Southeastern Asia, United Kingdom and Australia. No country may be considered free from fasciolosis risk.

Forecast for fasciolosis incidence will be increasing in the future continuing with a trend noticed in recent years, such trend which is due to climate change (Van Dijk et al, 2010.). The disease has been diagnosed in 29 states within Mexico, wherein prevalence is in the range from 2% up to 100%. Data collected in Mexico show that among 36 million bovines, 18 million are exposed to infection by *Fasciola hepatica*, since cattle is located in zones known as "fasciolosis-relevant" (Ibarra, 2000).

Relevance of this parasitosis resides in such large economic losses caused to livestock, due to a generally chronic liver and bile conduct inflammatory process, and also due to digestive and nutritional disorders. That above is translated into direct losses due to death of young animals by massive infections of *Fasciola hepatica*, and indirect losses due to seizures of livers at slaughterhouse, abortions, low growth and reproduction rate and also low meat, milk production, predisposition to their diseases, and expenses by treatment.

The main compounds used for treatment of fasciolosis are shown in Table I, and their activity spectrum against trematode at several ages is summarized in Table II. (Fairweather and Boray 1999).

TABLE I

Treatment with fasciolicides

| CHEMICAL GROUP | EXAMPLE |
|---|---|
| Halogenated phenols | Bithionol (Bitin, Actamer), Hexachlorophene (previously Bilevon, now obsolete), Niclofolan (Bilevon), nitroxynil (Trodax) |
| Salycylanilides | Brotianide (dirian), Closantel (Flukiver, Seponver, Supaverm, Cosicare), Oxyclozanide (Nilzan, Zanil), Rafoxanide (Flukanide, Ranizole). |
| Benzimidazoles | Albendazole (Valbazen), Mebendazole (Telmin, Vermox, Supaverm), Triclabendazole (Fasinex), Luxabendazole (Fluxacur). |
| Sulfonamides | Chlorsulon (Curatrem, Ivomec F, Ivomec Plus). |

TABLE II

Efficacy spectrum of drugs in recommended dose rates against *Fasciola hepatica* in sheep.

| DRUG | FASCIOLA AGE IN WEEKS | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Bithionol, Hexachlorophene, Oxyclozanide, Niclofolan, Albendazole, Closulon + Ivermectin (injection) | | | | | | | | | | 50-70% | | | 80-99% | |
| Closuron (oral) | | | | | | | | | | | 90-99% | | | |
| Nitroxynil, Closantel | | | | | | | | 50-90% | | | | | 91-99% | |
| Rafoxanide | | | | | 50-90% | | | | | | | 91-99% | | |
| Triclabendazole | 90-99% | | | | | | | | | | | 91-99% | | |
| Diamphenetide | 91-100% | | | | | | | | | | | 50-80% | | |

As noticed in above table II, albendazole, which was introduced in market in 1975, has been one of the most successful benzimidazole derivatives due to its high spectrum and high efficacy against gastrointestinal nematodes. However, it acts over *Fasciola hepatica* only on weeks 10-11, having a 50-70% efficacy; while in weeks 12-14 it shows 80-90% efficacy. Likewise, diamphenetide has 91 to 100% efficacy in 2-6 week juvenile *fasciola*, but not being effective in 7-week adult *fasciola*. The only fasciolicide acting in juvenile and adult stages is triclabendazole.

Recent studies demonstrate that in spite of the good fasciolicide activity features of orally administered triclabendazole, it has a significant drawback in being highly polar and very little soluble in biological fluids, as it is biotransformed in liver to form sulfoxide, this being a main metabolite showing fasciolicide activity, therefore being absorbed in only 5% of administered dose. In this context, triclabendazole is administered at a dose of 12 mg/Kg by weight in cattle, therefore 5400 mg of triclabendazole is needed for a 450 Kg bovine. Now, if 100 heads of cattle weighing an average of 450 Kg are available, 540,000 mg (540 g) of triclabendazole would be needed, and also when considered that only 5% is absorbed, then only 27 g of total administered weight to 100 heads of cattle would be absorbed, which represents a large loss in cost/profit.

As previously mentioned, plasma levels of triclabendazole as sulfoxide has been determined in other studies to be only of 5%, while the remaining is removed in feces (92%), in urine (2%) and in milk (1%), which pollute environment.

In spite of above, triclabendazole is still the drug of choice for treatment of liver trematode infections in cattle since almost 30 years, this being only orally administered.

Triclabendazole has been successfully used recently for treatment of fasciolosis in humans, showing high efficacy against adult and juvenile trematode located in biliary ducts and in liver parenchyma, respectively (Boray et al, 1983; (Smeal & Hall, 1983; Turner et al, 1984).

*ciola gigantica* (Hyman et al., 1984) and *Fascioloides magna* (Foreyt, 1989), though lacking activity against nematodes and cestodes, (Wolff et al, 1983; Güralp and Tinar, 1984; Coles, 1986).

It is known that triclabendazole interfers in tubulin polymerization inhibition to form nuclear microtubules, in addition to an additional proposed action inhibiting protein synthesis, causing parasite death by disorganization of support structure and formation of different organelles, e.g., Golgi complex.

One of the main problems of antihelmintic benzimidazoles in general is their low aqueous solubility, which leads to poor gastrointestinal absorption. This has led medicaments to be administered in formulations of suspensions, powders, pour-on and intra ruminal injection which are currently used.

An excessive use of triclabendazole as fasciolicide has caused resistance problems, which was firstly noticed in farm animals in Australia at mid-90's (Overend and Bowen, 1995) and it has been found since then in several European countries such as Ireland, United Kingdom, Netherlands and Spain (Fairweather, 2005).

A case of triclabendazole resistance in human being has been currently confirmed in Netherlands (Winkelhagen 2012).

On the other hand, the great dependency on triclabendazole to keep animal productivity and health puts in risk future treatment strategies.

In the light of above discussion, it can be clearly seen an urgent need of having alternative drugs with similar or higher efficacy than triclabendazole for controlling this parasitosis. A compound named "alpha compound" (5-Chloro-2-(methylthio)-6-(1-naphthyloxy)-1H-benzimidazole) was recently synthesized, which showed fasciolicide activity equivalent to triclabendazole (Hernandez-Campos 2008).

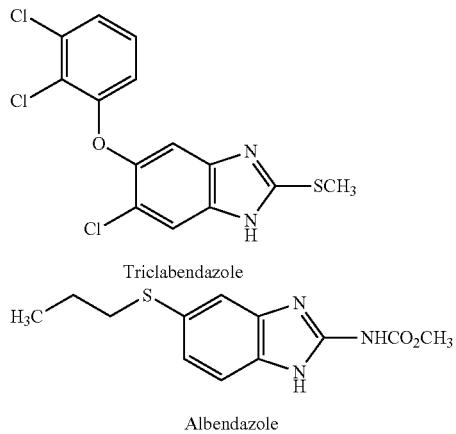

Triclabendazole

Albendazole

Benzimidazole-Type Compounds Used for Treatment of Fasciolosis

Triclabendazole differs structurally from albendazole and other methyl benzimidazole 2-carbamates, since it has a methylthio group at 2-position of benzimidazole nucleus, which in addition to 6-chloro and 5-dichlorophenoxy, confers higher liposolubility improving its biopharmaceutical properties, being very specific for *Fasciola hepatica, Fas-*

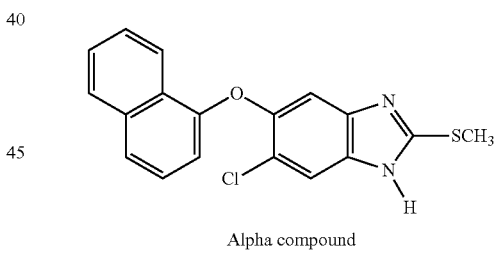

Alpha compound

Alpha compound (5-Chloro-2-(methylthio)-6-(1-naphthyloxy)-1H-benzimidazole)

"Alpha compound" is a triclabendazole bioisostere, with in-vitro and in-vivo fasciolicide activity, compared to that from triclabendazole, being useful in treatment of fasciolosis. However, as with triclabendazole, it shows a significant drawback of being hardly water-soluble, therefore its administration to animals is limited to oral route.

On the other hand, substitution of 1-position hydrogen of benzimidazole by a phosphonooxymethyl group for improving aqueous solubility of methyl benzimidazole 2-carbamates, has been already reported for phenbendazole and albendazole, and the like; as described in U.S. Pat. No. 7,893,271. It is worth to remark that said compounds are not fasciolicides.

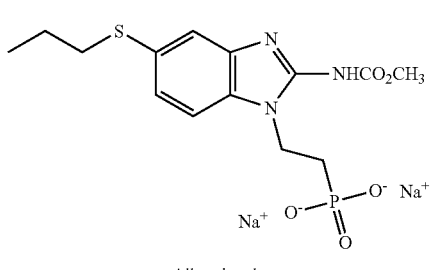

Albendazole

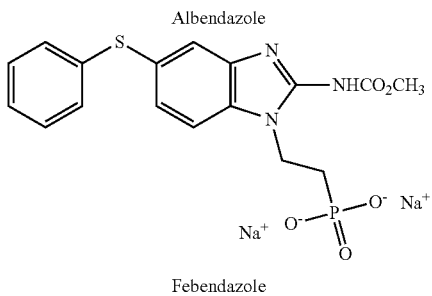

Febendazole

Examples of Compounds Protected Under U.S. Pat. No. 7,893,271

However, there is not any report describing the "alpha compound" or triclabendazole with a phosphonooxymethyl group at 1-position up to date.

Generally, as mentioned repeatedly in this section of Background of the Invention, benzimidazoles are poorly soluble in water, and because of that they are orally administered in the form of suspension, paste or powder, or instead, through intra ruminal injection, limiting significantly their applications.

In the light of all above discussion, there is not any benzimidazole-derived fasciolicide compound in the state of the art which is of broad spectrum, in addition to being effective in juvenile and adult stages, but specially, being highly hydrosoluble.

SUMMARY OF THE INVENTION

The present invention is related to novel hydrosoluble compounds derived from benzimidazole which are highly efficient in treatment of fasciolosis, which may be preferably administered by intramuscular route (injectable solution) due to their high solubility. Said compounds are represented by general formula I:

Formula (I)

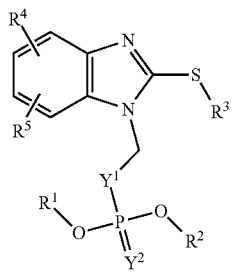

wherein:

$Y^1$ e $Y^2$ are independently O or S, and at least one of $Y^1$ and $Y^2$ is O;

$R^1$ and $R^2$ are independently hydrogen or a cation, both are hydrogen or both are cations;

$R^3$ is a C1-4 alkyl;

$R^4$ and $R^5$ are independently halogen or an —$OR^6$ alcoxide;

$R^6$ is C6-C10 aryl linked on 5- or 6-position of benzimidazole nucleus.

Present invention is also related to a pharmaceutical composition comprising a compound of general formula 1 and a pharmaceutically acceptable carrier.

OBJECTS OF THE INVENTION

Taking into account the drawbacks of prior art, it is an object of present invention to provide novel hydrosoluble compounds derived from benzimidazole which are highly efficacious in treatment and prophylaxis of fasciolosis.

It is a further object of the present invention to provide novel hydrosoluble compounds derived from benzimidazole, which are chemically stable and suitable for the same therapeutical applications than 2-(methylthio)-benzimidazoles.

A further object of present invention is to provide novel hydrosoluble compounds derived from benzimidazole which may be administered to domesticated and wild animals and also to humans, as those may be released by biological hydrolysis, therefore being considered as prodrugs.

Still another further object of the present invention is to provide novel hydrosoluble compounds derived from benzimidazole, which in addition to increase aqueous solubility, provide stability at physiological pH and high lability before alkaline phosphatases, so that they may be administered by several routes such as oral route, which may be formulated in the form of tablets, capsules, enteric coated capsules, bolus, as well as injectable solutions for administering by intramuscular route among other pharmaceutical forms.

Still another further object of the present invention is to provide a pharmaceutical composition including the novel hydrosoluble compounds derived from benzimidazole, which is useful for preparation of a medicament useful in veterinary and human medicine for treatment of fasciolosis, at lower doses than the pharmaceutical compositions found in the state of the art.

DETAILED DESCRIPTION OF THE INVENTION

Before an imperative need of providing new fasciolicides having better dissolution features, novel hydrosoluble compounds derived from benzimidazole having efficacious fasciolicide activity have been developed, further being highly soluble in aqueous medium, said compounds being described and claimed in the present invention.

The novel hydrosoluble compounds derived from benzimidazole are described in accordance with a particularly preferred embodiment of present invention, and these are pharmaceutically acceptable phosphonooxymethyl benzimidazole metal salts which may release the active principle known as "alpha compound" or triclabendazole, through biological hydrolysis reactions of alkaline estearases of treated animals, wherein said benzimidazole-derived novel compounds are represented by the following general formula I:

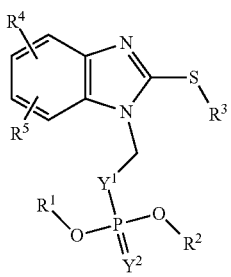

Formula I wherein:

$Y^2$ e $Y^2$ are independently O or S, preferably at least one of those two is O, and more preferably both are O.

Described compounds in the particularly preferred embodiment of present invention are N-phosphonooxymethyl substituted 2-(methylthio)benzimidazoles represented by general formula I, that is, compounds where $Y^2$ and $Y^2$ are O.

$R^1$ and $R^2$ are independently each other, hydrogen, a cation, both are hydrogen or both are cations. Preferably at least one is cation, and more preferably both are cations. The cation is selected from the group comprising: sodium, magnesium, manganese and ammonium; being sodium preferably selected as cation.

Hydrosoluble compounds disclosed in the particularly preferred embodiment of present invention include salts, where for example $R^1$ is H and $R^2$ is H, $R^1$ is H and $R^2$ is sodium. Salts are also included where $R^1$ and $R^2$ are sodium. Further are also included mixtures thereof, for example, mono- and di-sodium salts or pharmaceutically acceptable cations.

$R^3$ is a C1-4 alkyl, preferably methyl.

$R^4$ and $R^5$ are independently halogen or an —$OR^6$ alcoxide, wherein $R^6$ is preferably aryl, and more preferably a phenyl or naphthyl group, which may be substituted or unsubstituted, being preferred naphthyl ester compounds such as (5- and 6-Chloro, 5- and 6-(naphthalen-1-yloxy)-1-phosphonooxymethyl-2-(methylthio)-1H-benzimidazole, or mixtures thereof, and still more preferably salts thereof (N-phosphonooxymethyl substituted alpha compound) and phenyl esters such as (5- and 6-Chloro, 5- and 6-(2,3-dichlorophenoxy)-1-phosphonooxymethyl-2-(methylthio)-1H-benzimidazole or mixtures thereof, and most preferably salts thereof (N-phosphonooxymethyl substituted triclabendazole).

$R^4$ or $R^5$ are preferably Cl or alkoxides —$OR^6$ wherein $R^6$ is aryl, and linked at 5- or 6-position of benzimidazole nucleus. Aryl term of $R^6$ refers to an aromatic hydrocarbon group having from 6 to 10 carbon atoms such as phenyl or naphthyl, and may be optionally substituted by one or more substituents such as hydroxy, halogen, nitro, cyano, amino, alkyl, alkoxy, amino, provided that compound antiparasitic activity is not affected.

In the compounds disclosed in the preferred embodiment of present invention $R^6$ is a phenyl group, wherein said phenyl is substituted with two halo substituents at 2-,3- positions and comprising an unsubstituted naphthyl group.

Alkyl groups of $R^3$ may be linear or branched, selected from the group comprising: methyl, ethyl, n-propyl, isopropyl, butyl, sec-butyl, tert-butyl, and the like, and which may be optionally substituted, for example, with a halo substituent. Methyl is preferably selected in the compounds described in the preferred embodiment of present invention.

Some of the compounds represented by general formula I, in accordance with present invention, may be present as a mixture of regioisomers. For example, a mixture of compounds may be synthesized where $R^4$ is linked at 5-position of benzimidazole nucleus producing a regioisomer, and another at 6-position of benzimidazole nucleus obtaining another regioisomer, respectively. In addition to pure regioisomers, such mixture comprising different regioisomers of course is part of the present invention.

Hydrosoluble compounds which are described and claimed in present invention are highly efficient as fasciolicides, and they are especially suitable to be preferably administered by intramuscular route (injectable solution) due to their high solubility, even when they may be also administered by any other suitable route such as oral route, and they may be formulated as tablets, capsules, enteric coated capsules, bolus.

Hydrosoluble compounds of present invention may be used alone as the sole active ingredient in a pharmaceutical composition, or instead, together with other therapeutic agents. The pharmaceutical composition is prepared according to the standard procedures used in veterinary or human medicine, wherein said pharmaceutical composition comprises an effective amount of one or more hydrosoluble compounds according to the present invention.

Furthermore, the hydrosoluble compounds of present invention may comprise any pharmaceutically acceptable aid, such as a carrier, a stabilizer or other excipients, and optionally comprise other therapeutic agents.

Hydrosoluble compounds derived from benzimidazole which are described in the present invention may be prepared by a known process of synthesis, which is described in the following Scheme 1:

Scheme 1

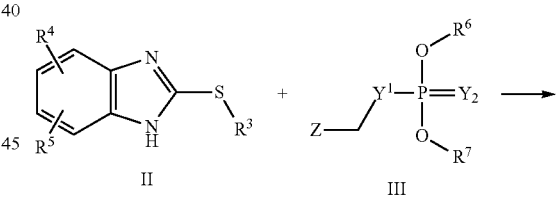

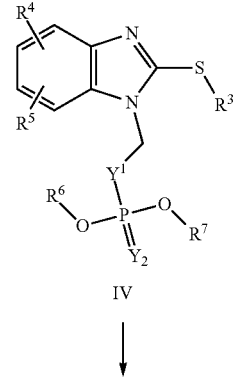

-continued

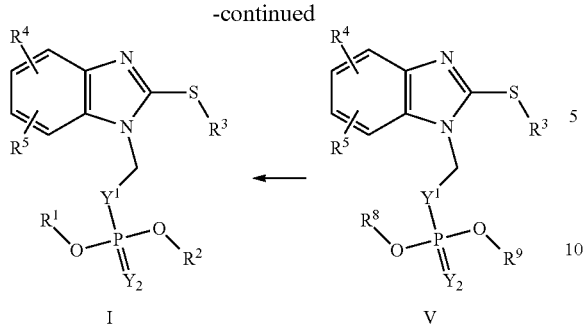

Synthesis process comprises the following steps.

(a) Reacting a functionalized suitable salt of 2-(methylthio)benzimidazole, wherein said salt is selected from the group comprising sodium, magnesium, manganese, ammonium, or a pharmaceutically acceptable salt, preferably using sodium as cation, with a phosphoric acid (III) diester substituted with a methylene group having a pendant group, Z such as chlorine, bromine, iodine, tosilate or mesylate to provide a compound of formula IV, wherein $R^6$ and $R^7$ are protective groups.

Suitable protective groups are known by those skilled in the art and may consist of, for example, an alkyl such as tert-butyl, phenyl or benzyl. This kind of phosphate (III) may be prepared by applying procedures available in literature (e.g., Tetrahedron Letters; 2002, 43, 3793 with an amendment). Formation of a (methylthio)benzimidazole alkaline salt may be achieved by addition of a base selected from sodium hydroxide, potassium hydroxide, sodium hydride or potassium hydride, preferably sodium hydride, to methylthiobenzimidazole (II) at a temperature range comprised between 0 and 30° C., in a suitable solvent, preferably an organic solvent selected from N,N-dimethylformamide, N,N-dimethylacetamide, N-methylpyrrolidone, N-ethylpyrrolidine, tetrahydrofuran or dioxanes, preferably using N,N-dimethylformamide. Reaction of the salt thus obtained with the phosphate triester (III) may be carried out at temperatures comprised between 0 and 80° C., preferably between 10 and 50° C. Depending on reaction temperature, reaction time may vary between 1 and 24 hours.

(b) Hydrolysing intermediate products (IV) to provide compounds V, wherein $R^8$ and $R^9$ are hydrogen, by an addition of an acid selected from acetic acid, trifluoroacetic acid or hydrochloric acid, preferably using hydrochloric acid, optionally in an organic solvent selected from diethyl ether, tetrahydrofuran, dioxane or dichloromethane, preferably using dioxane, at a temperature in the range from 25 to 50° C.

(c) Converting isolated products (V) to their corresponding salts I, where at least one between $R^1$ and $R^2$ are the sodium salt, by addition of a base selected from sodium alkoxide, sodium hydroxide, potassium alkoxide, potassium hydroxide or ammonia, preferably sodium hydroxide. The reaction may be carried out in water or organic solvent selected from methanol, ethanol, isopropanol, tert-butanol, or mixtures thereof, preferably using methanol.

The present invention will be better understood from the following examples, which are included only for illustrative purposes in order to allow a full understanding of the embodiments of the present invention, without implying that other non-illustrated embodiments are not absent which may be put into practice based on above made detailed description.

Example 1.—Synthesis of "Alpha Compound" Hydrosoluble Derivative

Synthesis of 5-Chloro-6-(naphthalen-1-yloxy)-1-phosphonooxymethyl-2-(methylthio)-1H-benzimidazole and 6-Chloro-5-(naphthalen-1-yloxy)-1-phosphonooxymethyl-2-(methylthio)-1H-benzimidazole.

Step A:

Synthesis of di-tert-butylchloromethyl phosphate III (Scheme 2)

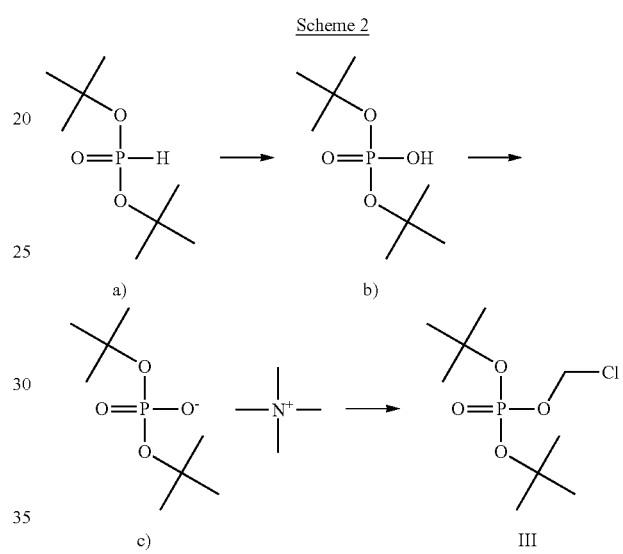

Synthesis of di-tert-butyl monoacid phosphate (b)

A mixture of 0.78 ml (0.78 g, 4 mmol) of di-tert-butyl phosphonate (a), 0.2 g (2.4 mmol) of $NaHCO_3$ and 4 ml of deionized water are stirred at 0° C. in an ice bath, once temperature is reached it is reacted for 20 minutes, then 0.44 g (2.8 mmol) of $KMnO_4$ are divided in 3 equal parts and added every 20 minutes to the reaction. A brown precipitate is formed ($MnO_2\downarrow$) and is left under stirring at room temperature for one hour. The reaction mixture is suction filtered and the residue is washed with 4 ml of deionized water. The filtrate is discolored with 0.06 g of activated carbon during 15 minutes at 60° C., then vacuum filtered over a celite bed and washed with 4 ml of deionized water. The translucent filtrate is cooled in an ice-water bath, 0.78 ml (0.78 g, 4 mmol) of concentrated HCl is added and cold stirred during 10 minutes. Formed white solid is separated by vacuum filtration, washed with 4 ml of cold deionized water and air dried. The crude product thus obtained is dissolved in chloroform, dried with anhydrous $Na_2SO_4$, filtered and vacuum concentrated. 0.754 g (89%) of a white color solid corresponding to compound b is obtained. NMR $^1H$ (DMSO-$d_6$, 300 MHz, δ ppm): 1.38 (s, 18H); NMR $^{13}C$ (DMSO-$d_6$, 75 MHz, δ ppm): 29.67 (d, J=4.3 Hz), 79.58 (d, J=6.9 Hz); NMR $^{31}P$ (CDCl$_3$, 300 MHz, δ ppm): −9.03 (s).

Synthesis of Di-tert-butyl Tetramethylammonium Phosphate (c)

A suspension of 0.75 g (3.57 mmol) of di-tert-butyl monoacid phosphate (b) and 5 ml of acetone is stirred in an ice-water-salt bath during 20 minutes with vigorous stirring. 0.97 ml (3.57 mmol) of tetramethylammonium hydroxide (tetramethylammonium hydroxide is taken from a 25% water solution) is slowly added, and left stirring at room temperature during 30 minutes. The solvent is then removed under reduced pressure thus forming a resinous semi-solid. Then, 10 ml of hexane is added, the mixture is placed under refrigeration during 24 hours. 0.87 g (87%) of a white solid corresponding to compound c is obtained. NMR $^1$H (DMSO-$d_6$, 300 MHz, δ ppm): 1.25 (s, 18H), 3.14 (s, 12H); NMR $^{13}$C (DMSO-$d_6$, 75 MHz, δ ppm): 30.29 (d, J=4.2 Hz), 54.30 (t, J=4.1 Hz), 72.79 (d, J=7.2 Hz); NMR $^{31}$P (CDCl$_3$, 300 MHz, δ ppm): −7.79 (s).

Synthesis of di-tert-butylchloromethyl phosphate (III)

A suspension of 0.87 g (3.08 mmol) of di-tert-butyl tetramethylammonium phosphate (b), 0.896 g (12.34 mmol) of NaHCO$_3$ in 26 ml of deionized water and 0.104 g (0.3 mmol) of TBAHS (tetrabutylammonium monoacid sulfate), is stirred in an ice-water bath for 10 minutes. 16 ml of CH$_2$Cl$_2$ is added and slowly 0.38 ml (0.6 g, 3.69 mmol) of chloromethyl chlorosulfate in 10 ml of CH$_2$Cl$_2$. The reaction mixture is left under stirring during 24 hours at room temperature. Phases are separated, and the organic phase is washed with NaCl saturated solution, with 5 ml of a 2% NaHCO$_3$ solution and with 5 ml of deionized water. It is dried with anhydrous Na$_2$SO$_4$ and concentrated in a rotary evaporator under reduced pressure. 0.71 g (89%) of a light yellow oil is obtained, corresponding to compound III. NMR $^1$H (CDCl$_3$, 300 MHz, δ ppm): 1.49 (d, 18H, J=0.7 Hz), 5.66 (d, 2H, J=14.9 Hz); NMR $^{13}$C (CDCl$_3$, 75 MHz, δ ppm): 29.83 (d, J=4.3 Hz), 73.3 (d, J=7.0 Hz), 84.2 (d, J=7.9 Hz); NMR $^{31}$P (CDCl$_3$, 300 MHz, δ ppm): −11.86 (s).

Step B:

Synthesis of [6-chloro-2-methylthio-5-(1-naphthyloxy)-1H-benzimidazole-1-yl]methyl di-tert-butyl phosphate (Compound 1) and [5-chloro-2-methylthio-6-(1-naphthyloxy)-1H-benzimidazole-1-yl]methyl di-tert-butyl phosphate (Compound 2)

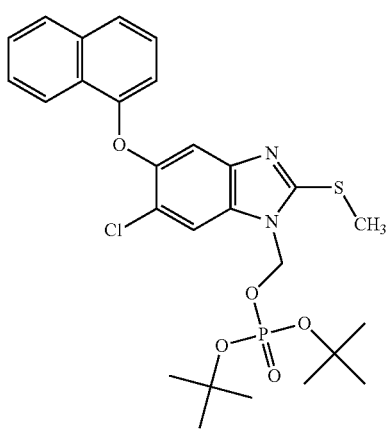

1

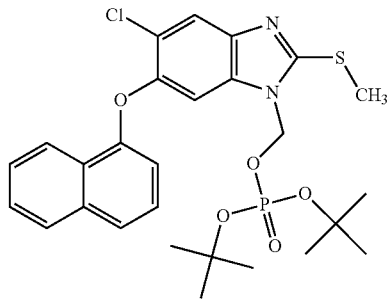

2

A mixture of 2 g (5.868 mmol) of alpha compound, 0.824 g (20.26 mmol) of NaH (60% suspension in mineral oil) and 20 ml of DMF are stirred during 1 hour at room temperature, then 1.972 g (7.628 mmol) of di-tert-butylchloromethyl phosphate is added in 5 ml of the same solvent, stirred during 24 hours at room temperature. Formed supernatant solid is removed by vacuum filtration, the residue washed with 5 ml of DMF and the filtrate is concentrated under reduced pressure until dryness. The resinous solid obtained is dissolved in a 50:50 AcOEt-Petroleum ether mixture and the solution is passed through a column 20-cm height by 1.5 diameter packed with 10 g of silica gel and washed with 100 ml of 50:50 AcOEt-Petroleum ether mixture, then with 100 ml of diethyl ether. Collected fractions are concentrated under reduced pressure in the rotary evaporator and the obtained resin shows two spots in equivalent proportion and little of raw material which was not consumed. The residue is treated with a mixture of Hexane-AcOEt (85:15), stirred in an ice-water bath and 1.2 g (36.6%) is separated of a white solid with a 130-130.5° C. melting point, corresponding to compound 2. NMR $^1$H (300 MHz, DMSO-$d_6$, δ ppm): 1.25 (s, 18H), 2.79 (s, 3H), 5.88 (d, 2H, J=11 Hz), 6.69 (d, 1H, J=7.6 Hz), 7.41 (t, 1H, J=8.0 Hz); 7.50 (s, 1H); 7.61-7.67 (m, 2H), 7.71 (d, 1H, J=8.3 Hz), 7.93 (s, 1H), 8.00-8.05 (m, 1H), 8.28-8.31 (m, 1H). $^{13}$C NMR (75 MHz, DMSO-$d_6$, δ ppm): 14.96, 29.63 (d, J=4.2 Hz), 68.85 (d, J=5.8 Hz), 83.25 (d, J=7.3 Hz), 104.49, 110.47, 119.37, 120.62, 121.69, 123.17, 125.36, 126.34, 126.72, 127.39, 128.29, 134.96, 135.65, 140.74, 146.97, 153.60, 155.82; $^{31}$P NMR (122 MHz, DMSO-$d_6$, δ ppm): −11.78; (EMAR-ES+) HRMS-ES+ Calculated for $C_{27}H_{33}N_2O_5PSCl$ 563.1563 found 563.1553.

Step C:

Synthesis of [6-chloro-2-(methylthio)-5-(naphthalen-1-yloxy)-1H-benzimidazole-1-yl]methyl dihydrogen phosphate (Compound 3) and [5-chloro-2-(methylthio)-6-(naphthalen-1-yloxy)-1H-benzimidazole-1-yl]methyl dihydrogen phosphate (Compound 4)

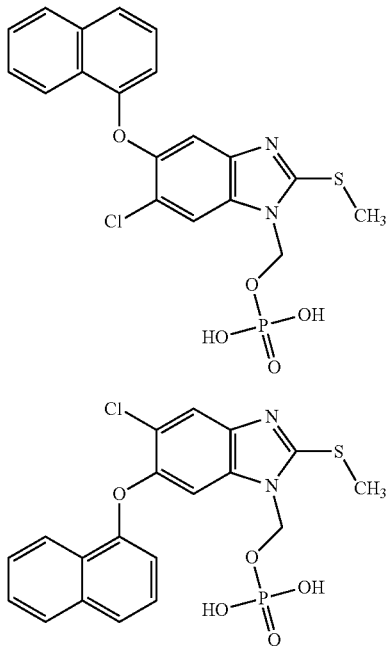

A suspension of 1.2 g (2.13 mmol) of compound 2, 3 ml of dioxane and 3 mL of a 4N HCl solution in dioxane is vigorously stirred during 24 hours with nitrogen atmosphere. White precipitate is filtered and washed with cold dioxane. The filtrate is concentrated until half-volume in a rotary evaporator. 0.86 g (90%) of acid (compound 4) is obtained with a melting point of 136-137° C. NMR $^1$H (300 MHz, DMSO-$d_6$, δ ppm): 2.77 (s, 3H); 5.84 (d, 2H, J=9.3 Hz), 6.60 (d, 1H, J=7.6 Hz), 7.38 (t, 1H, J=8.0 Hz), 7.61-7.67 (m, 4H), 7.89 (s, 1H), 7.98-8.01 (m, 1H), 8.32-8.35 (m, 1H). $^{13}$C NMR (75 MHz, DMSO-$d_6$, δ ppm): 15.02, 68.46 (d, J=3.3 Hz), 105.50, 109.46, 119.07, 121.10, 121.74, 122.73, 125.08, 126.45, 126.64, 127.38, 128.23, 134.87, 135.56, 140.39, 146.45, 153.91, 155.98; $^{31}$P NMR (122 MHz, DMSO-$d_6$, δ ppm): −2.75; (EMAR-ES+) HRMS-ES+ Calculated for $C_{19}H_{17}N_2O_5SClP$ 451.0284 found 451.0269.

Washings of Hexane-AcOEt containing the other regioisomer (compound 1) are concentrated to dryness and subject to acidic hydrolysis as described above. 0.8 g of a white solid, corresponding to compound 3 is obtained. NMR $^1$H (300 MHz, DMSO-$d_6$, δ ppm): 2.74 (s, 3H), 5.91 (d, 2H, J=9.3 Hz), 6.64 (d, 1H, J=7.6 Hz), 7.38 (t, 1H, J=8.0 Hz), 7.41 (s, 1H), 7.58-7.67 (m, 3H), 7.95 (s, 1H), 7.96-7.99 (m, 1H), 8.23-8.26 (m, 1H). $^{13}$C NMR (75 MHz, DMSO-$d_6$, δ ppm): 14.86, 68.38 (d, J=5.8 Hz), 110.15, 111.25, 112.34, 120.19, 121.83, 122.69, 125.27, 126.47, 126.63, 128.28, 133.69, 134.94, 142.92, 147.10, 153.81, 156.10; $^{31}$P NMR (122 MHz, DMSO-$d_6$, δ ppm): −2.62; (EMAR-ES+) HRMS-ES+ Calculated for $C_{19}H_{17}N_2O_3SClP$ 451.0284 found 451.0269.

Step D:

Synthesis of [6-chloro-2-(methylthio)-5-(naphthalen-1-yloxy)-1H-benzimidazole-1-yl]methyl disodium phosphate (Compound 5), and [6-chloro-2-(methylthio)-5-(naphthalen-1-yloxy)-1H-benzimidazole-1-yl]methyl disodium phosphate (Compound 6)

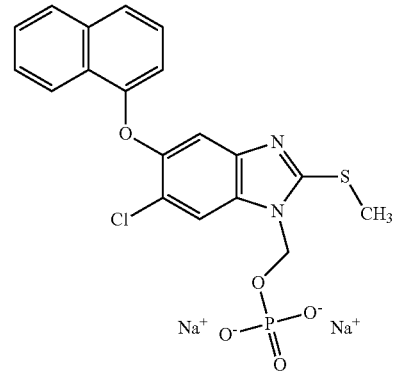

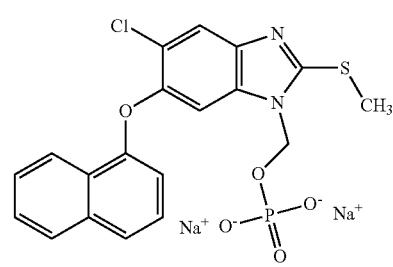

A suspension of 0.5 g (1.11 mmol) of the mixture (compounds 3 and 4) and 5 ml of MeOH are stirred during 10 minutes, a 0.1N solution of MeONa/MeOH is added dropwise with vigorous stirring until reaching a pH of 11. The solution is concentrated to dryness under reduced pressure. 0.5 g (90%) of the isomer mixture is obtained (compounds 5 and 6). NMR $^1$H (300 MHz, $D_2O$, δ ppm): 2.57 (s, 3H), 5.55 (d, 2H, J=4.4 Hz), 6.75 (d, 1H, J=7.7 Hz); 7.38 (t, 1H, J=8.9 Hz); 7.36 (s, 1H), 7.49-7.58 (m, 3H), 7.68 (d, 1H, J=8.3 Hz), 7.68 (s, 1H), 7.90-7.93 (m, 1H), 8.22-8.25 (m, 1H). $^{13}$C NMR (75 MHz, $D_2O$, δ ppm): 14.96, 29.63 (d, J=4.2 Hz), 68.85 (d, J=5.8 Hz), 83.25 (d, J=7.3 Hz), 104.49, 110.47, 119.37, 120.62, 121.69, 123.17, 125.36, 126.34, 126.72, 127.39, 128.29, 134.96, 135.65, 140.74, 146.97, 153.60, 155.82; $^{31}$P NMR (122 MHz, $D_2O$, ppm): −1.55; (EMAR-ES+) HRMS-ES+ Calculated for $C_{19}H_{24}N_2O_5Na_3SClP$ 516.9743 found 516.9767.

Example 2.—Synthesis of Triclabendazole Hydrosoluble Compound

Step B:

Synthesis of [6-chloro-2-methylthio-5-(2,3-dichlorophenoxy)-1H-benzimidazole-1-yl] methyl di-tert-butyl phosphate (Compound 7) and [6-chloro-2-methylthio-5-(2,3-dichlorophenoxy)-1H-benzimidazole-1-yl] methyl di-tert-butyl phosphate (Compound 8)

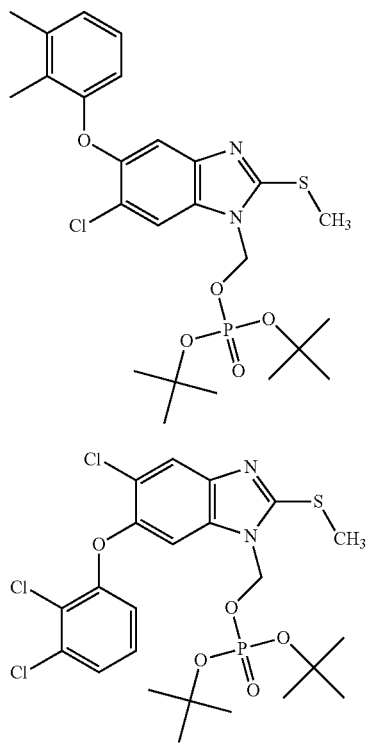

7

8

A mixture of 2 g (5.56 mmol) of triclabendazole, 0.79 g (19.46 mmol) of NaH (60% suspension in mineral oil) and 20 ml of DMF are stirred during 1 hour at room temperature; then 1.868 g (7.228 mmol) of di-tert-butylchloromethyl phosphate in 5 ml of the same solvent are added and stirred during 24 hours. The obtained resin is dissolved in 50:50 AcOEt-Petroleum ether mixture and the solution is passed through a 20-cm height by 1.5 diameter column packed with 10 g of silica gel and is washed with 100 ml of 50:50 AcOEt-Petroleum ether mixture and then with 100 ml of diethyl ether.

Collected fractions are concentrated under reduced pressure in the rotary evaporator, the obtained resin shows two spots in similar proportion and some raw material which was not consumed. Obtained resin is treated with a mixture of Hexane-AcOEt (85:15), stirred in an ice-water bath and precipitated a white solid, which is separated by suction filtration. This product results by TLC (thin layer chromatography) a mixture of regioisomers with 164-165° C. melting point. NMR $^1$H (300 MHz, DMSO-$d_6$, δ ppm): 1.30 (s, 18H), 1.36 (s, 18H), 2.77 (s, 3H), 2.78 (s, 3H), 5.91 (d, 2H, J=1 Hz), 5.98 (d, 2H, J=11 Hz), 6.66 (dd, 1H, J=8.4, 1.4 Hz), 6.73 (dd, 1H, J=8.3, 1.4 Hz), 7.27-7.35 (m, 2H); 7.40-7.45 (m, 2H); 7.40 (s, 1H), 7.52 (s, 1H), 7.88 (s, 1H), 7.90 (s, 1H). $^{13}$C NMR (75 MHz, DMSO-$d_6$, δ ppm): 14.86, 14.94, 29.69 (t, J=4.2 Hz), 68.85 (t, J=5.8 Hz), 83.25 (t, J=7.3 Hz), 104.33, 104.33, 119.79, 120.20, 125.25, 129.19, 133.45, 133.47, 134.02, 135.60, 141.08, 142.85, 145.94, 146.10, 154.71, 154.94, 156.21, 156.52; $^{31}$P NMR (122 MHz, DMSO-$d_6$, 5 ppm): −11.46, −11.69; (EMAR-ES+) HRMS-ES+ Calculated for $C_{23}H_{29}N_2O_5PSCl_3$ 581.0600 found 581.0587

Step C:

Synthesis of [6-chloro-2-(methylthio)-5-(2,3-dichlorophenoxy)-1H-benzimidazole-1-yl]methyl dihydrogen phosphate (Compound 9) and [6-chloro-2-(methylthio)-5-(2,3-dichlorophenoxy)-1H-benzimidazole-1-yl]methyl dihydrogen phosphate (Compound 10)

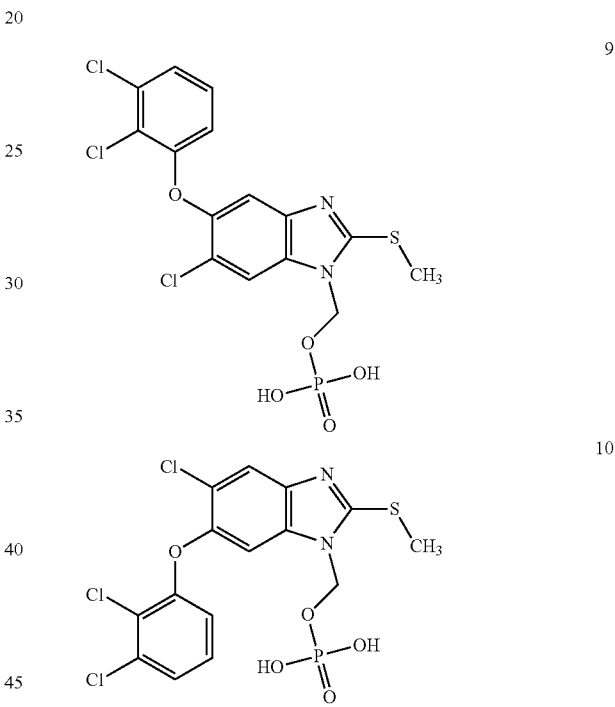

9

10

A suspension of 1.2 g (2.13 mmol) of compounds 7 and 8, 3 ml of dioxane and 3 ml of a 4N HCl solution in dioxane is vigorously stirred during 30 minutes, the white precipitate thus formed is separated by vacuum filtration and the residue washed with cold dioxane. The filtrate is concentrated to half volume and a white solid is generated, which is separated by filtration and washed with dioxane. 0.86 g (90%) of acid (compound 10) is obtained with a 200-201° C. melting point. NMR $^1$H (300 MHz, DMSO-$d_6$, δ ppm): 2.73 (s, 3H), 2.75 (s, 3H), 5.83 (d, 2H, J=9.5 Hz), 5.88 (d, 2H, J=9.5 Hz), 6.63-6.67 (m, 2H), 6.24-6.29 (m, 2H) 7.37-7.40 (m, 2H), 7.50 (s, 1H), 7.59 (s, 1H), 7.86 (s, 1H), 7.89 (s, 1H). $^{13}$C NMR (75 MHz, DMSO-$d_6$, δ ppm): 14.87, 14.91, 68.39 (t, J=3.2 Hz), 105.20, 111.28, 112.45, 115.34, 115.67, 119.36, 119.84, 120.35, 124.82, 124.94, 124.99, 129.21, 129.24, 133.35, 133.40, 134.09, 135.70, 141.31, 142.86, 145.37, 146.01, 154.99, 156.28, 156.42; $^{31}$P NMR (122 MHz, DMSO-$d_6$, δ ppm): −2.57, −2.64; (EMAR-ES+) HRMS-ES+ Calculated for $C_{15}H_{13}N_2O_5PSCl_3$ 468.9348 found 468.9348.

Step D:

Synthesis of [6-chloro-2-(methylthio)-5-(2,3-dichlorophenoxy)-1H-benzimidazole-1-yl]methyl disodium phosphate (Compound 11) and [6-chloro-2-(methylthio)-5-(2,3-dichlorophenoxy)-1H-benzimidazole-1-yl]methyl disodium phosphate (Compound 12)

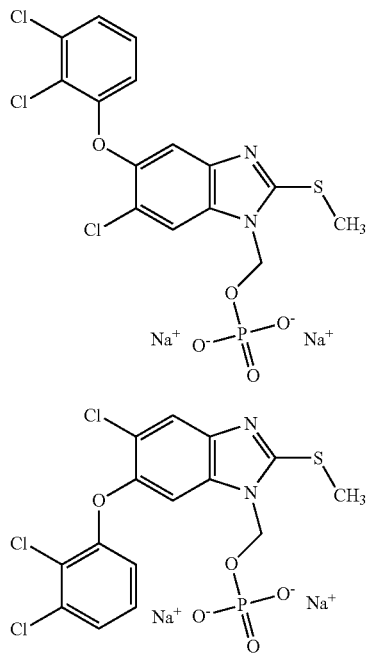

A suspension of 0.5 g (1.11 mmol) of compounds 9 and 10, and 5 mL of MeOH is stirred during 10 minutes, then a 0.1N MeONa/MeOH solution is added dropwise under vigorous stirring until reaching a pH of 11. The solution is concentrated under reduced pressure and 0.5 g (90%) of compounds 11 and 12 is obtained. NMR $^1$H (300 MHz, D$_2$O, δ ppm): 2.61 (s, 3H), 2.64 (s, 3H), 5.57 (d, 2H, J=9.5 Hz), 5.66 (d, 2H, J=9.5 Hz), 5.60 (d, 1H, J=9.5, 1.2 Hz), 5.67 (d, 1H, J=9.3 Hz), 7.06 (td, 2H); 7.38 (dd, 2H), 7.21 (s, 1H), 7.36 (s, 1H), 7.64 (s, 1H), 7.78 (s, 1H). $^{13}$C NMR (75 MHz, D$_2$O, δ ppm): 14.87, 14.91, 68.39 (t, J=3.2 Hz), 105.20, 111.28, 112.45, 115.34, 115.67, 119.36, 119.84, 120.35, 124.82, 124.94, 124.99, 129.21, 129.24, 133.35, 133.40, 134.09, 135.70, 141.31, 142.86, 145.37, 146.01, 154.99, 156.28, 156.42; $^{31}$P NMR (122 MHz, D$_2$O, ppm): −2.57, −2.64; (EMAR-ES+) HRMS-ES+ Calculated for C$_{15}$H$_{13}$N$_2$O$_5$PSCl$_3$ 468.9348 found 468.9348.

Studies of Aqueous Solubility:

Solubility of "alpha compound" (4) and hydrosoluble derivative (7) was determined in three copies and individually by the method reported by Yalkowski. Sample was prepared by addition in excess of the compound to be tested (4=10 mg; 7=167 mg) in an aqueous solution at pH 7 (10 mL) contained in a capped tube. Sample was stirred at room temperature for 48 hours until reaching equilibrium between the two phases. The tube was then centrifuged at 4500 rpm for minutes at room temperature. Compound 4 solution was separated from the solid and its concentration was determined in a spectrophotometer at 305 nm. Meanwhile, clear solution of compound 7 was separated from solid residue and 1 mL diluted in water at 100 mL. Its concentration was then determined in a spectrophotometer at 350 nm. Concentration corresponding to solubility was determined by using a calibration curve in the range of 0.2-1.2 μg/mL obtaining the following results:

TABLE 1

| Prodrug 7 aqueous solubility and chemical stability | | |
|---|---|---|
| Compound | Aqueous solubility (mg/mL)$^a$ pH 7 | Aqueous solubility (h)$^b$ pH 7 |
| 7 | 13.0 | >26 |
| Alpha compound | 2.6 × 10$^{-4}$ | >26 |
| TCBZ$^c$ | 2.0 × 10$^{-4}$ | >24 |

$^a$Determined at 25° C.,
$^b$>95% by UV-HPLC determined at room temperature,
$^c$TCBZ solubility reported in literature.

Aqueous solubility of "alpha compound" (4), determined as 2.6×10$^{-4}$ mg/mL, was substantially increased by the compound or prodrug 7 with the introduction of a phosphonooxymethyl group, the latter with a solubility of 13 mg/mL at pH 7 (Table 1), demonstrating an increase of 50,000 times aqueous solubility in respect of its parent compound 4. This result is consistent with previous reports that prodrug design, such as 7, is successful in increasing aqueous solubility in non-polar drugs.

Stability Studies:

A solution of compound 4, TCBZ and compound 7, was prepared at a concentration of 1 mg/mL. In case of compounds 4 and TCBZ the suspension was filtered through a WHATMAN 25 mm GD/X CA filter; filtrates and compound 7 solution were diluted with 5 mL of water. Solutions were kept at room temperature (25° C.) for 26 hours (24 hour for TCBZ), and 5 mL of the samples were later diluted in 10 mL of water and analyzed by UV-HPLC. Stability of compounds 4, TCBZ and 7 was determined by comparison of signal areas corresponding to compounds at zero time (t0) and 24 hours after incubation. Retention time for compound or prodrug 7 is 1.5 minutes, while retention time for "alpha compound" is 3 minutes.

In prodrug formulation, the compound should also demonstrate suitable chemical stability, especially in parenteral dosage forms. Compound 7 showed the intended stability (>95% after 26 hours) at neutral pH, which is ideal for formulation from a physiological point of view.

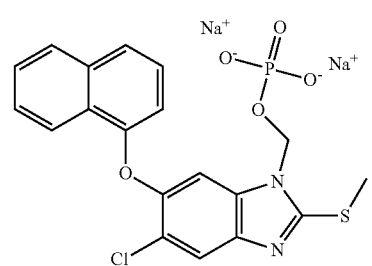
7a

7b

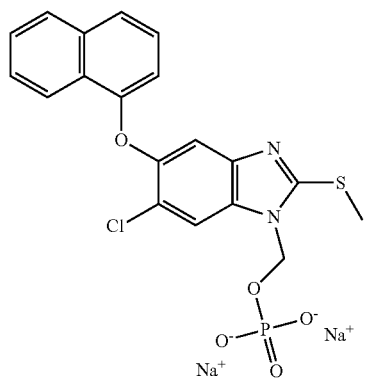

In Vivo Studies:

Evaluation was carried out in 24 native sheep of any sex, between 10 and 12 months old, free of F. hepatica infection, animals were experimentally infected by oral route with 200 parasite metacercaria per sheep. Said metacercaria were obtained from laboratory-infected Lymnaea humilis snails with bovine-origin miracidia. The compound or prodrug 7 (7a and 7b) was administered in a single dose by several routes of administration 12 mg/Kg/orally, 4 mg/Kg/intramuscularly and 4 mg/Kg/subcutaneously. Samples from feces were taken from all sheep during days 0, 95 and 105 post-treatment in order to positively diagnose to F. hepatica eggs using a sedimentation technique. At 15 days post-treatment, all ovine were sacrificed in order to remove their liver to collect and count the number of vermises present, determining the percentage of trematode reduction in treated groups in relation to the number of parasites present in the control group. Efficacy is determined according to the following formula.

% Eficacy={[Average eggs or fasciola in control group–Average eggs or fasciola in treated group]/[Average eggs or fasciola in control group]}×100

Compound 7 was evaluated in vivo against F. hepatica, observing a reduction of fasciola in the three routes of administration. Obtained results showed 83.3%, 87.8% and 61.4 efficacies by oral, intramuscular and subcutaneous route respectively using different concentrations (see Table 2). Fasciolicide activity of alpha compound was determined in previous studies, resulting that a dose of 15 mg/Kg obtained 86.9% efficacy against mature and juvenile fasciola. With that above fasciolicide efficacy of compound or prodrug 7 administered by intramuscular route is observed to increase compared to "alpha compound".

TABLE 2

Efficacy of compound 7 measured as percentage of reduction of vermises and eggs of F. hepatica in experimentally infected ovine

| Group and route of administration (n = 6) | Dose (mg/Kg/) | Average ± SD | | Efficacy (%) | |
|---|---|---|---|---|---|
| | | Egg reduction | Fasciola reduction | Egg reduction | Fasciola reduction |
| 1 (oral) | 12 | 3.6 ± 1.5 | 12.3 ± 2.3 | 95.1 | 83.3 |
| 2 (intramuscular) | 4 | 35.7 ± 5.6 | 9.0 ± 1.2 | 44.9 | 87.8 |
| 3 (subcutaneous) | 4 | 23.0 ± 4.3 | 28.5 ± 3.4 | 65.8 | 61.4 |
| 4 (control group) | Without treatment | 76.3 ± 8.9 | 74.0 ± 9.2 | 0 | 0 |

In-Vitro Evaluation of "Alpha Compound" Fasciolicide Efficacy:

In order to evaluate the anti-fasciola effect of compounds 5 and 6 as mixture of regioisomers, artificially excysted fasciola were used (approximately six hours after excystment), according to the disclosure by Ibarra and Jenkins, (1984). Briefly, recently excysted fasciola are suspended in 90 ml of Roswell Park Memorial Institute (RPMI)-1640® culture media plus 90 ml of bovine serum and 1.5 ml of antibiotics (Penicillin and Streptomycin) at a density of 100 individuals/ml.

Compound Preparation.—

5 mg of experimental compound was used and placed in a universal bottle (30 ml capacity), to which 0.1 ml of methanol was added to dissolve the compound. From this point, required dilutions are carried out with distilled water to prepare concentrations of 50 and 10 mg/l.

In-Vitro Evaluation.—

24-well NUNC® culture dishes were used and 1.6 ml of culture medium (RPMI/bovine serum), 0.2 ml of the compound concentration to be tested and 0.2 ml of RPMI containing 10 fasciola per well are placed into each well. Control wells which contain fasciola without compound are used per each dish, further including a control group with a reference drug (Triclabendazole-Fasinex®-Novartis). Each concentration is carried out three times. Each sample remains under incubation at 37° C. during 4 days under a 5% $CO_2$ atmosphere.

Test Interpretation.—

Fasciola under study are examined at 24, 48 and 72 hours post-exposure to compound through an inverted microscope at 40×. Extract activity is measured by comparing survival of treated fasciola with control group fasciola. All procedures are carried out under aseptic conditions in a laminar flow hood.

Efficacy Measurement.—

Efficacy is measured by using the following formula (Abbott, 2004):

% Efficacy=[Fasciola in control group–Fasciola in treated group]/[Fasciola in treated group]

The extract is considered to have fasciolicide activity when showing an in vitro efficacy higher than 80%. (Ibarra & Jenkins, 1984; Elango & Rahuman, 2011; Ibarra et al, 2013).

Results:

Gathered information may be appreciated in general in the following table:

| Concentration | EFFICACY (%) | | | | Standard |
|---|---|---|---|---|---|
| (mg/l) | 1st Test | 2nd Test | 3rd Test | Average± | Deviation |
| Mortality percentage at 24 hours post-exposure of alpha compound-soluble against *Fasciola hepatica* under in vitro conditions | | | | | |
| Alpha (50) | 100 | 100 | 100 | 100 | 0 |
| Alpha (10) | 100 | 87.5 | 100 | 95.83 | 0.0722 |
| TCB (50) * | 100 | 100 | 100 | 100 | 0 |
| TCB (10) * | 100 | 100 | 100 | 100 | 0 |
| Control without Tx. ** | — | — | — | — | — |
| Mortality percentage at 48 hours post-exposure of alpha compound-soluble against *Fasciola hepatica* under in vitro conditions | | | | | |
| Alpha (50) | 100 | 100 | 100 | 100 | 0 |
| Alpha (10) | 100 | 87.5 | 100 | 95.83 | 0.0722 |
| TCB (50) * | 100 | 100 | 100 | 100 | 0 |
| TCB (10) * | 100 | 100 | 100 | 100 | 0 |
| Control without Tx. ** | — | — | — | — | — |
| Mortality percentage at 72 hours post-exposure of alpha compound-soluble against *Fasciola hepatica* under in vitro conditions | | | | | |
| Alpha (50) | 100 | 100 | 100 | 100 | 0 |
| Alpha (10) | 100 | 87.5 | 100 | 100 | 0 |
| TCB (50) * | 100 | 100 | 100 | 100 | 0 |
| TCB (10) * | 100 | 100 | 100 | 100 | 0 |
| Control without Tx. ** | — | — | — | — | — |

\* = Triclabendazole (Fasinex ®-Novartis) as reference control.

\*\* = Control without treatment.

Discussion.—

Collected information, though preliminary, clearly indicates that the "soluble alpha compound" is highly efficient against *Fasciola hepatica*, and compared to triclabendazole (acknowledged as the best worldwide fasciolicide), shows that on third day post-exposure 100% of mortality or efficacy was reached.

Conclusion.—

"Solubilized alpha compound" showed high fasciolicide efficacy (100%) at 72 hours post-exposure against recently excysted *fasciola* under in vitro conditions. Even though above description has been referred to certain embodiments of hydrosoluble compounds derived from benzimidazole of present invention, it should be emphasized that possible modifications to such embodiments are possible, such as the use of different cations or solvents used in said compound synthesis, and the like, but without being apart from the true scope of the invention. Therefore, the present invention shall not be restricted except for the contents in the state of the art and the attached claims.

The invention claimed is:

1. Hydrosoluble compounds derived from benzimidazole represented by general formula I:

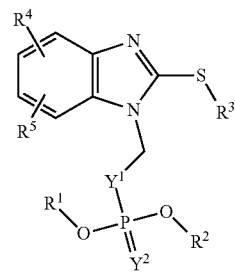

Formula (I)

wherein:

$Y^1$ and $Y^2$ are independently O or S, and at least one of $Y^1$ and $Y^2$ is O;

$R^1$ and $R^2$ are independently hydrogen or a cation, both are hydrogen or both are cations;

$R^3$ is a C1-4 alkyl;

$R^4$ and $R^5$ are independently halogen or an —$OR^6$ alkoxide; and $R^6$ is C6-C10 aryl linked at 5- or 6-position of benzimidazole nucleus.

2. The hydrosoluble compounds derived from benzimidazole according to claim 1, wherein $Y^1$ and $Y^2$ both are O.

3. The hydrosoluble compounds derived from benzimidazole according to claim 1, wherein at least one of $R^1$ and $R^2$ is a cation.

4. The hydrosoluble compounds derived from benzimidazole according to claim 1, wherein $R^1$ and $R^2$ both are cations.

5. The hydrosoluble compounds derived from benzimidazole according to claim 3, wherein the cation comprises at least one of sodium, magnesium, manganese and ammonium.

6. The hydrosoluble compounds derived from benzimidazole according to claim 5, wherein the cation is sodium.

7. The hydrosoluble compounds derived from benzimidazole according to claim 1, wherein $R^1$ and $R^2$ both are hydrogen.

8. The hydrosoluble compounds derived from benzimidazole according to claim 1, wherein $R^1$ is hydrogen and $R^2$ is sodium.

9. The hydrosoluble compounds derived from benzimidazole according to claim 1, wherein $R^3$ is methyl.

10. The hydrosoluble compounds derived from benzimidazole according to claim 1, wherein at least one of $R^4$ or $R^5$ is chlorine.

11. The hydrosoluble compounds derived from benzimidazole according to claim 1, wherein $R^6$ is a substituted or unsubstituted phenyl or naphthyl group.

12. The hydrosoluble compounds derived from benzimidazole according to claim 11, wherein $R^6$ is a phenyl group substituted with two halo substituents at 2,3-positions.

13. The hydrosoluble compounds derived from benzimidazole according to claim 11, wherein $R^6$ is an unsubstituted naphthyl group.

14. The hydrosoluble compounds derived from benzimidazole according to claim 1, wherein the alkyl group of $R^3$ is linear or branched and is selected from methyl, ethyl, n-propyl, isopropyl, butyl, sec-butyl, and tert-butyl.

15. The hydrosoluble compounds derived from benzimidazole according to claim 14, wherein the alkyl group is methyl.

16. The hydrosoluble compounds derived from benzimidazole according to claim 1, wherein said compounds are a mixture of regio-isomers in which $R^4$ is linked at 5-position of benzimidazole nucleus originating in a first regio-isomer and another at 6-position of benzimidazole nucleus originating in another regio-isomer.

17. The hydrosoluble compounds derived from benzimidazole according to claim 1, wherein the hydrosoluble compounds are adapted for intramuscular administration.

18. The hydrosoluble compounds derived from benzimidazole according to claim 1, wherein the hydrosoluble compounds are in a form of tablets, capsules, enteric coated capsules, or a bolus.

19. A pharmaceutical composition comprising:
a compound as claimed in claim 1; and,
a pharmaceutically acceptable vehicle.

20. The pharmaceutical composition of claim 19, wherein the pharmaceutical composition is adapted for veterinary or human use to treat fasciolosis.

\* \* \* \* \*